United States Patent [19]

McKinnie et al.

[11] Patent Number: 4,602,113

[45] Date of Patent: * Jul. 22, 1986

[54] (HYDROCARBYLTHIO) PHENOLS AND THEIR PREPARATION

[75] Inventors: Bonnie G. McKinnie, Magnolia, Ak.; Paul F. Ranken, Baton Rouge, La.

[73] Assignee: Ethyl Corporation, Richmond, Va.

[*] Notice: The portion of the term of this patent subsequent to Aug. 6, 2002 has been disclaimed.

[21] Appl. No.: 551,336

[22] Filed: Nov. 14, 1983

Related U.S. Application Data

[63] Continuation-in-part of Ser. No. 484,338, Apr. 12, 1983, Pat. No. 4,533,753.

[51] Int. Cl.$^4$ .................. C07C 148/00; C07C 149/36
[52] U.S. Cl. ...................................................... 568/54
[58] Field of Search ..................................... 568/54, 47

[56] References Cited

U.S. PATENT DOCUMENTS

| | | | |
|---|---|---|---|
| 2,259,861 | 10/1941 | Richardson | 568/54 X |
| 2,745,878 | 5/1956 | Mavity | 568/54 |
| 2,831,898 | 4/1958 | Ecke et al. | 260/624 |
| 2,923,743 | 2/1960 | Delfs et al. | 568/54 |
| 2,923,745 | 2/1960 | Buls et al. | 260/624 |
| 3,134,818 | 5/1964 | Farah et al. | 568/54 |
| 3,149,139 | 9/1964 | Meisert | 568/54 X |
| 3,200,157 | 8/1965 | Buls et al. | 260/624 |
| 3,246,040 | 4/1966 | Reifschneider | 568/54 X |
| 3,274,257 | 9/1966 | Reifschneider et al. | 568/54 X |
| 3,303,209 | 2/1967 | Reifschneider et al. | 260/465 F |
| 3,335,190 | 8/1967 | Du Bois et al. | 568/54 |
| 3,629,225 | 12/1971 | Allphin, Jr. | 252/45 X |
| 3,655,773 | 4/1972 | Reifschneider | 568/45 |
| 3,714,264 | 1/1973 | Spacht | 568/54 |
| 3,723,538 | 3/1973 | Bissinger et al. | 568/54 |
| 3,728,399 | 4/1973 | Spacht | 568/47 |
| 3,912,782 | 10/1975 | Kiel et al. | 568/54 X |
| 4,120,866 | 10/1978 | Winkler | 568/54 X |
| 4,128,530 | 10/1978 | Cottman | 568/54 X |
| 4,324,920 | 4/1982 | McKinnie et al. | 568/54 |

FOREIGN PATENT DOCUMENTS

| | | | |
|---|---|---|---|
| 2055770 | 11/1970 | Fed. Rep. of Germany | 568/54 |
| 0875464 | 8/1961 | United Kingdom . | |
| 0953834 | 4/1964 | United Kingdom | 568/54 |
| 0964225 | 7/1964 | United Kingdom . | |

OTHER PUBLICATIONS

Trost, et al., Chemical Abstracts, vol. 89, 197093z (1978).
Goethals, et al., Chemical Abstracts, vol. 61, 10614a-e, (1964), note 10614e.
Scheinpflug, et al., Chemical Abstracts, vol. 65, 13543c (1966), note attached Subject Index, p. 16,907s, "phenol, 2,4,6-trichloro-3-(methylthio)".
Farah, et al., J. Organic Chem., vol. 28, (1963), pp. 2807-2809, "Alkyl-Mercaptophenols by Sulfenylation of Phenols".
Pederson, et al., Tetrahedron, vol. 26, (1970), pp. 4449-4457, "o-Hydroxyphenyl Alkyl Sulfides, Sulfoxides and Sulfones".
Cabiddu, et al., Gazetta Chimica Italiana, vol. 99, No. 4, pp. 397-410, (1969).

*Primary Examiner*—Donald G. Daus
*Assistant Examiner*—Diana G. Rivers
*Attorney, Agent, or Firm*—Donald L. Johnson; John F. Sieberth; Patricia J. Hogan

[57] ABSTRACT (Hydrocarbylthio)phenols containing hydrocarbylthio groups in either or both of the meta positions, relative to the hydroxy group, on a phenolic ring are prepared by reacting phenolic compounds with an excess of hydrocarbyl disulfide in the presence of catalytic amounts of an aluminum phenoxide. Novel and useful (hydrocarbylthio)phenols containing hydrocarbylthio groups in either of both of the meta positions, relative to the hydroxy group, on a phenolic ring can be prepared by this process. (Hydrocarbylthio)phenols containing hydrocarbylthio groups in either of both of the meta positions, relative to the hydroxy group, on a phenolic ring are effective antioxidants for organic material normally susceptible to oxidative deterioration, such as mineral oil.

11 Claims, No Drawings

(HYDROCARBYLTHIO) PHENOLS AND THEIR PREPARATION

REFERENCE TO RELATED APPLICATION

This application is a continuation-in-part of our copending application Ser. No. 484,338, filed Apr. 12, 1983 now U.S. Pat. No. 4,533,753.

INTRODUCTION

This invention relates to novel and useful (hydrocarbylthio)phenols.

BACKGROUND OF THE INVENTION

Ortho-(hydrocarbylthio)phenols are useful compounds, e.g., as intermediates in the preparation of hypotensive drugs and agricultural chemicals such as plant protection agents, herbicides, pesticides and the like. U.S. Pat. No. 2,923,743 describes a process for the production of aryl-alkyl thioethers by reacting a dialkyl disulfide with aromatic compounds such as phenol, chlorophenol, p-cresol, 2-naphthol, etc., in the presence of suitable condensation agents, such as for example, aluminum chloride, aluminum bromide, ferric chloride, zinc chloride, tin tetrachloride, antimony pentachloride, boron fluoride and bleaching earth. At Column 1, lines 31–36, that patent discloses:

"These condensation agents can be added in different amounts. In general there should be added at least molecular amounts referred to the dialkyl disulfide but there can be used also higher amounts e.g. a 3-fold surplus of the condensation agent."

U.S. Pat. No. 3,246,040 discloses the synthesis of certain substituted phenolic compounds containing two alkylthio groups and from 0 to 3 halo or nitro groups. This patent discloses that the compounds are useful as pesticides; as inhibitors of the germination of fungus spores, they are effective fungistats. They are also useful as intermediates in the preparation of biologically active materials such as organic phosphates.

In our U.S. Pat. No. 4,324,920 and our reissue application Ser. No. 430,553, filed Sept. 30, 1982, the disclosures of which are incorporated herein by reference, we disclose a process for the preparation of ortho-(hydrocarbylthio)phenols by contacting phenols, having at least one hydrogen on a carbon atom ortho to a hydroxy group, with hydrocarbyl disulfides in the presence of catalytic amounts of aluminum phenoxide.

In our copending application Ser. No. 484,338, filed Apr. 12, 1983, the disclosure of which is incorporated herein by reference, we disclose novel and useful (hydrocarbylthio) phenols containing at least two hydrocarbylthio groups and a process for their preparation.

SUMMARY OF THE INVENTION

It has been found that hydrocarbylthio-substituted phenols, wherein the phenolic compound is substituted by a hydrocarbylthio group in either or both of the meta positions relative to the hydroxy group, can be prepared in good yields by contacting phenols, having either or both meta positions available for substitution on a phenolic ring, with an excess of hydrocarbyl disulfides in the presence of catalytic amounts of aluminum phenoxide. An excess of hydrocarbyl disulfide is defined to be a quantity of hydrocarbyl disulfide greater than the stoichiometric amount required for the number of hydrocarbylthio groups desired in the (hydrocarbylthio)phenol. A catalytic amount of aluminum phenoxide means less than molecular or equivalent amounts of aluminum phenoxide. The process ot this invention requires no solvent and makes use of cheap and available materials. Still further advantages will be apparent from the following disclosure.

It has also been found pursuant to this invention that novel and useful products can be produced by the foregoing process. Compounds of the invention are represented by Formula I:

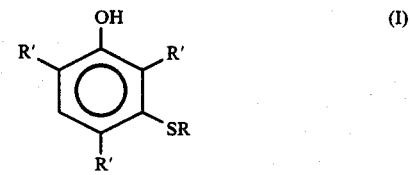

wherein the R' groups are chlorine, fluorine, or the same or different hydrocarbyl groups.

Additional compounds of the invention are represented by Formula II:

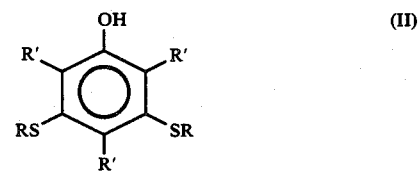

wherein the R' groups are chlorine, fluorine, or the same or different hydrocarbyl groups.

Further compounds of the invention are represented by Formula III:

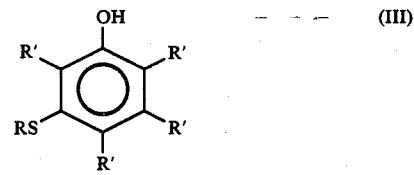

wherein the R' groups are chlorine, fluorine, or the same or different hydrocarbyl groups.

In Formulas I, II, and III, the R groups are hydrocarbyl groups which may differ but which preferably are the same in any given compound. R may be, for example, an aryl group, an alkyl group or a cycloalkyl group typically having up to about 10 carbon atoms, such as phenyl, methyl, ethyl, propyl, n-butyl, sec-butyl tert-butyl, hexyl, octyl, decyl, cyclopropyl, cyclopentyl, cyclohexyl, cycloheptyl, cyclooctyl, cyclopropylcarbinyl, and the like. Preferably R is an alkyl group containing up to about 4 carbon atoms, most preferably methyl or ethyl.

The R' hydrocarbyl groups of Formulas I, II and III are either saturated aliphatic or cycloaliphatic groups or are aromatic groups. In most cases they will be: alkyl of 1 to 50 carbon atoms; cycloalkyl of from 3 to 20 carbon atoms; aryl of from 6 to 12 carbon atoms; alkaryl of from 7 to 20 carbon atoms; and aralkyl of from 7 to 20 carbon atoms.

The compounds of this invention are useful antioxidants. The compounds of this invention will provide protection against oxidative deterioration of an organic material or substrate that is normally susceptible to oxidative deterioration. Such protection is provided when a (hydrocarbylthio)phenol, substituted by a hydrocarbylthio group in either or both of the meta positions relative to the hydroxyl group, is present in the organic material in a small amount sufficient to inhibit such deterioration, generally about 0.05–5.0 weight percent.

DETAILED DESCRIPTION OF THE INVENTION

Process

In accordance with one aspect of this invention there is provided a process for the preparation of hydrocarbylthio-substituted phenols, wherein the phenolic compound is substituted by a hydrocarbylthio group in either or both of the meta positions relative to the hydroxyl group, which comprises contacting (i.e., reacting) phenols, having either or both meta positions available for substitution on a phenolic ring, with an excess of a hydrocarbyl disulfide in the presence of an aluminum phenoxide catalyst, the molar ratio of the catalyst to the disulfide being less than 1, preferably between about 0.002 and 0.3 and most preferably between about 0.01 and 0.1. The process is normally conducted at a temperature within the range of from about 0° C. to about 300° C. at which the desired reaction takes place. Preferably the process is performed at a temperature of from about 100° C. to about 300° C. and most preferably from about 100° C. to about 200° C. With the process of this invention one mole of hydrocarbylthiol (RSH) is formed as by-product for each hydrocarbylthio group (RS—) substituted onto the phenol. Without being bound to a particular mechanism or theory, it appears that the reacting hydrocarbyl disulfide is split into two species or moieties, one being substituted onto the phenol the other forming the corresponding hydrocarbylthiol by-product. In a particularly preferred embodiment, the process of this invention is conducted in such a way that the hydrocarbylthiol by-product is removed from the reaction vessel essentially as rapidly as it is formed. This can be accomplished for example by conducting the reaction at reflux temperature and/or under reduced pressures (i.e. below atmospheric pressure) and/or under a sweep of an inert gas so that the hydrocarbylthiol by-product evolved is rapidly removed or purged from the reaction vessel. Alternatively, the reaction may be carried out at pressures greater than one atmosphere with the hydrocarbylthiol by-product being removed by distillation.

In still another preferred embodiment of this invention the hydrocarbyl disulfide reactant is a saturated aliphatic or cycloaliphatic hydrocarbyl disulfide, most preferably a lower alkyl disulfide.

The aluminum phenoxide catalyst used in the practice of this invention can be formed in various ways. For example it can be formed by contacting aluminum metal, preferably in the form of turnings, powders, particles and the like, with the phenol at elevated temperatures (e.g. 100-200° C.) until cessation of hydrogen evolution. Another way of forming the catalyst used in this invention is by simply contacting an aluminum alkyl such as triethylaluminum with the phenol. Still another method of forming the catalyst used herein involves contacting aluminum chloride (i.e. AlCl$_3$) and the phenol at elevated temperatures, e.g. between 100 and 200° C., and purging the system of the hydrogen chloride generated during the preparation of the phenoxide catalyst. The source of the aluminum phenoxide catalyst does not materially affect the reaction and other methods known in the art for the formation of these compounds can be successfully employed herein. Exemplary methods for preparing aluminum phenoxide catalysts useful in the process of this invention appear in U.S. Pat. Nos. 2,831,898, 2,923,745 and 3,200,157. The preferred catalyst is aluminum triphenoxide, although a diphenoxide catalyst, e.g., diphenoxyaluminum chloride (which may be formed in the reaction of aluminum chloride and phenol) or diphenoxyaluminum: hydroxide (which may be formed by reaction of aluminum chloride and phenol containing small amounts of water), can also be used in the practice of this invention.

Hydrocarbyl disulfides which may be employed in the practice of this invention include the aromatic disulfides, the alkyl disulfides and the cycloalkyl disulfides, these respective disulfides preferably having up to about 10 carbon atoms in each aryl, alkyl or cycloalkyl group. Preferably the hydrocarbyl disulfide is a lower alkyl disulfide, i.e., an alkyl disulfide in which each alkyl group contains 1 to about 6 carbon atoms, such as, for example, methyl disulfide and ethyl disulfide, these two compounds being particularly preferred reactants because of their availability and good reactivity in the process. Unsaturated aliphatic disulfides, unsaturated cycloaliphatic disulfides, as well as substituted hydrocarbyl disulfides, may be used provided they do not interfere with the reaction. However, if the final product is to be used as an antioxidant in lubricating oils, it is preferred that the product be essentially halogen-free. Hydrocarbyl disulfides which may be used herein include, for example, phenyl disulfide, methyl disulfide, ethyl disulfide, methyl ethyl disulfide, n-butyl disulfide, sec-butyl disulfide, tert-butyl disulfide, propyl disulfide, cyclopentyl disulfide, cyclohexyl disulfide, cycloheptyl disulfide and the like. When it is desired to introduce two different -SR groups into the product, two different hydrocarbyl disulfides will normally be employed in the reaction, either simultaneously or consecutively. The total quantity of the two disulfides used will be in excess of the stoichiometric amount required to introduce the number of -SR groups desired in the product.

The phenols used herein are 2,4,6-trisubstituted phenols or 2,3,4,6-tetrasubstituted phenols. The substituents in the 2-, 3-, 4- and 6- positions should be relatively inert under the conditions of the reaction. For example, the substituents may be chlorine, fluorine, alkyl, aryl, aralkyl, alkaryl, cycloalkyl, alkoxy, and the like. If the final product is to be used as an antioxidant in lubricating oils, it is preferred that the product be formed from a phenolic compound that is essentially halogen free.

Those skilled in the art will appreciate that factors of steric hindrance and the relative position of the substituent(s) on the ring should be taken into account when determining what substituents may be present in the starting phenolic compound. Also, since some tertiary aliphatic groups ortho to an aromatic hydroxy group may undergo dealkylation, aliphatic groups in the ortho position(s) are preferably secondary aliphatic groups, and most preferably are primary aliphatic groups.

The class of phenolic reactants for use in the process are those which can be presented by Formula IV:

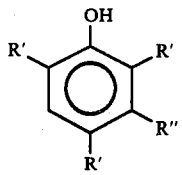

(IV)

wherein the R' groups are chlorine, fluorine, or the same or different hydrocarbyl groups and R" is hydrogen, chlorine, fluorine, or the same or different hydrocarbyl groups. Typically, each R' and R" hydrocarbyl group will be essentially devoid of olefinic and acetylenic unsaturation and usually will contain no more than about 50 carbon atoms. Thus, the R' and R" groups may be an alkyl group having from 1 to about 50 or more (and preferably from 1 to about 20) carbon atoms, such as, for example, methyl, ethyl, propyl, isopropyl, tert-butyl, pentyl, heptyl, eicosyl, triacontyl, pentacontyl and the like; an aryl group having from 6 to about 12 carbon atoms, such as, for example, phenyl, 4-biphenylyl, 1-naphthyl, and the like; an aralkyl group having from about 7 to about 20 carbon atoms, such as, for example, benzyl, phenylethyl (phenethyl), phenylhexyl, phenylheptyl, phenyloctyl, phenylnonyl, phenylundecyl, phenyldodecyl, phenyltridecyl, phenyltetradecyl, phenylcyclopropyl, phenylcyclohexyl, 2,4-dimethylbenzyl, and the like; an alkaryl group having from about 7 to about 20 carbon atoms, such as, for example, tolyl, xylyl, mesityl, butylphenyl, iso-butylphenyl, sec-butylphenyl, tert-butylphenyl, ethylphenyl, pentylphenyl, 4-methylbiphenyl, 3-methylbiphenyl and the like; and a cycloalkyl group having from 3 to about 20 carbon atoms, such as, for example, cyclopropyl, cyclohexyl, cyclooctyl, bicyclohexyl, butylcyclohexyl, methylcyclohexyl, cyclobutyl, cyclodecyl, cyclododecyl, cyclohexylphenyl, cyclopentyl, and the like, as well as other hydrocarbyl groups exemplified by cyclopropylphenyl, α-cyclopropylphenylmethyl and the like. However, the tri- and tetra-substituted phenols wherein the substituent in the 4- position is a long chain alkyl group, made by alkylating substituted phenols with propylene oligomers or isobutylene oligomers of molecular weights as high as 10,000, may be used. Of these long chain substituted phenols, it is preferred that the long chain alkyl group has from about 50 to about 700 carbon atoms.

Some examples of the phenolic compounds represented by Formula IV include but are not limited to: 2,4,6-trimethylphenol, 2,4,6-triethylphenol, 2,4,6-tripropylphenol, 2,4,6-tricyclopropylphenol, 2,4,6-trihexylphenol, 2,4,6-trichlorophenol, 3-chloro2,4,6-trimethylphenol, and the like.

A particularly preferred embodiment of this invention involves reaction of (i) a phenol of Formula IV above wherein the R" is hydrogen and the R' groups are alkyl groups of from 1 to about 4 carbon atoms with (ii) a lower alkyl disulfide, i.e., each alkyl group has from 1 to about 6 carbon atoms, using an aluminum phenoxide catalyst in the manner described above. It is especially desirable to perform these embodiments under conditions whereby the alkyl mercaptan by-product is removed from the reaction mixture during the course of the reaction.

In practicing the process of this invention the hydrocarbyl disulfide is normally added to the phenol-aluminum phenoxide mixture although the order of addition is not critical. Once the phenol and hydrocarbyl disulfide have been contacted in the presence of the catalyst the reaction is allowed to proceed at temperatures and times which can vary depending upon such considerations as the boiling point of the hydrocarbylthiol generated during reaction, the percent yield of product desired, the melting point of the reactants and the like. In general, when the reaction is carried out at atmospheric pressure, temperatures slightly above the boiling point of the hydrocarbyl disulfide are employed. In a particularly preferred aspect, the mixture is maintained at or near its reflux temperature. Of course if pressures below atmospheric pressure are employed the corresponding temperature may also be decreased. In a preferred embodiment as much of the hydrocarbylthiol by-product as is feasible is removed, e.g. by vacuum distillation and the like. Total reaction times of more than one day are typically employed when the reaction is run at atmospheric pressure. However, if desired, the reaction may be conducted at pressures greater than atmospheric pressure with provision being made for removal of the hydrocarbylthiol by-product and thereby shorter reaction times may be employed.

In practicing this invention a broad range of proportions of reactants can be utilized. That is, the relative molar amounts of phenol to the disulfide can vary widely; however, the relative proportions employed normally fall within the range of from about 1:2.1 to about 1:20, and most preferably within the range of from about 1:2.5 to about 1:6. Furthermore, while the process of this invention can be carried out without the use of solvents or diluents they may nevertheless be used, if desired, so long as they are inert to the reaction disclosed herein. Hydrocarbons and ethers are illustrative of the solvents that may be employed. The process is preferably carried out under substantially anhydrous conditions, but conditions wherein trace or small amounts of water are present can be used. Accordingly, an inert atmosphere is normally employed in the present process.

Compounds

As noted above, another aspect of this invention involves the provision of novel and useful compounds producible by the process described above. These compounds are depicted hereinabove in Formulas I, II and III.

Illustrative examples of compounds which are provided in accordance with this invention include but are not limited to such compounds as the following:

Formula I 2,4,6-trimethyl-3-(methylthio)phenol,
2,4,6-trimethyl-3-(ethylthio)phenol,
2,4,6-trimethyl-3-(propylthio)phenol,
2,4,6-trimethyl-3-(butylthio)phenol,
2,4,6-triethyl-3-(methylthio)phenol,
2,4,6-triethyl-3-(ethylthio)phenol,
2,4,6-triethyl-3-(propylthio)phenol,
2,4,6-triethyl-3-(butylthio)phenol,
2,4,6-tributyl-3-(methylthio)phenol,
2,4,6-tributyl-3-(ethylthio)phenol,
2,4,6-tributyl-3-(propylthio)phenol,
2,4,6-tributyl-3-(butylthio)phenol,
2,4,6-trichloro-3-(methylthio)phenol,
2,4,6-trichloro-3-(ethylthio)phenol,
2,4-dimethyl-6-chloro-3-(methylthio)phenol,
2,4-dimethyl-6-chloro-3-(ethylthio)phenol, and 2,6-dimethyl-4-sec-eicosyl-3-(methylthio)phenol.

Formula II 2,4,6-trimethyl-3,5-bis(methylthio)phenol,
2,4,6-trimethyl-3,5-bis(ethylthio)phenol,
2,4,6-triethyl-3,5-bis(methylthio)phenol,
2,4,6-triethyl-3,5-bis(ethylthio)phenol,
2,4,6-triethyl-3,5-bis(propylthio)phenol,
2,4,6-tripropyl-3,5-bis(methylthio)phenol,
2,4,6-tributyl-3,5-bis(methylthio)phenol,
2,4,6-trichloro-3,5-bis(methylthio)phenol,
2,4,6-trichloro-3,5-bis(ethylthio)phenol,
2,4-dimethyl-6-chloro-3,5-bis(methylthio)phenol,
2,4-dimethyl-6-chloro-3,5-bis(ethylthio)phenol, and
2,6-dimethyl-4-octadecyl-3,5-bis(methylthio)phenol.

Formula III 2,4,6-trimethyl-3-chloro-5-(methylthio)phenol,
2,4,6-trimethyl-3-chloro-5-(ethylthio)phenol,
2,3,4,6-tetramethyl-5-(methylthio)phenol, and
2,3,4,6-tetramethyl-5-(ethylthio)phenol.

The preparation of the compounds of this invention will be still further apparent from the following illustrative example which is not intended to limit the invention in any manner.

In the Example, the reaction was carried out under nitrogen in a 3-neck round bottom flask equipped with a magnetic stirring bar, thermometer, and a Vigreux column. On top of the Vigreux column was a reflux condenser.

Distillations were performed using a 6-inch Vigreux column.

Further, VPC analyses were performed using a 10 foot OV-101 (6%) column programmed from 100° C. to 280° C. at 10° C. per minute.

EXAMPLE

Reaction of 2,4,6-Trimethylphenol and Dimethyl Disulfide

To 10.6g (0.078 mole) of 2,4,6-trimethylphenol was cautiously added, in a nitrogen atmosphere, 1.3 ml (0.005 mole) of triisobutylaluminum. The stirred mixture was heated to 100° and 15 ml (0.166 mole) of methyl disulfide was added. The reaction was then stirred at reflux. Analysis by gas chromatography of an acid-quenched sample showed a composition, after 1 day at reflux, of 86 area % 2,4,6-trimethylphenol and 12 area % 2,4,6-trimethyl-3(methylthio)phenol. Another 7 ml (0.077 mole) of methyl disulfide was added and reflux was continued. An analysis after 24 hours (2 days total) showed 30 area % 2,4,6-trimethylphenol and 66 area % 2,4,6-trimethyl-3(methylthio)phenol. The reaction was refluxed for an additional 5 days (7 days total), cooled, treated with 50 ml 0.1 N HCl and extracted 4×50 ml CH$_2$Cl$_2$. The combined extracts were concentrated on a rotary evaporator to give a black oil. Gc analysis showed 7 area % 2,4,6-trimethylphenol, 54 area % 2,4,6-trimethyl-3(methylthio)phenol and 6 area % 2,4,6-trimethyl-3,5-bis(methylthio)phenol. Mass spectroscopy confirmed the identity of the compounds.

Utility

The compounds of this invention are useful as antioxidants in a variety of organic materials when present in the organic material in effective concentrations, usually concentrations below about 5% by weight of the organic material, preferably within the range of from about 0.05% by weight to about 1% by weight and more preferably within the range of from about 0.25% by weight to about 0.75% by weight, typically about 0.5% by weight. As is well understood in the art, the particular concentration of an antioxidant employed will be governed to some extent by the nature of the substrate and the type and severity of the storage and service conditions to which the substrate will be exposed. Thus when using the compounds of this invention as antioxidants, the amounts may be varied to suit the needs of the occasion.

The substrates that may be protected by means of the antioxidant compounds of this invention include a broad range of organic materials of the type normally subject to oxidative deterioration in the presence of oxygen during storage or use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not flame retarding agents nor flame suppressing additives and the degradation protected against is not combustion but, rather, the gradual deterioration of the organic composition due to the effects of oxygen over an extended period of time.

Examples of organic materials in which the additives, i.e. the products of this invention may be useful include homopolymers and copolymers of olefinically unsaturated monomers, for example, polyolefins such as polyethylene, polypropylene, polybutadiene, and the like. Also, poly-halohydrocarbons such as polyvinyl chloride, polychloroprene, polyvinylidene chloride, polyfluoro olefins, and the like, are afforded stabilization. The additives may provide both antioxidant and antiozonate protection in natural and synthetic rubbers such as copolymers of olefinically unsaturated monomers including styrene-butadiene rubber (SBR rubber), ethylene-propylene copolymers, ethylene-propylene-diene terpolymers such as the terpolymer of ethylene, propylene and cyclopentadiene or cyclooctadiene. Polybutadiene rubbers such as cis-polybutadiene rubber may be protected. Poly-2-chloro-1,3-butadiene (neoprene) and poly-2-methyl-1,3-butadiene (isoprene rubber) may be stabilized by the present additives. Likewise, acrylonitrile-butadiene-styrene resins and polystyrenes (both crystal grades and rubber modified grades) are effectively stabilized. Ethylene-vinyl acetate copolymers may be protected, as are butene-methylacrylate copolymers. Nitrogen-containing polymers such as polyurethanes, nitrile rubber, and lauryl acrylate-vinylpyrrolidone copolymers may be effectively stabilized. Adhesive compositions such as solutions of polychloroprene (neoprene) in toluene may be protected.

Petroleum oils and waxes such as solvent-refined midcontinent lubricating oil, microcrystalline wax, and Gulf-coast lubricating oils are effectively stabilized. The additives may be useful in foamed plastics such as expanded polystyrene, polyurethane foams, and the various foamed rubbers, alkyd resins such as short oil terephthalic acid-glycerol-linseed oil resins, and resins including epoxide-modified alkyl resins. Epoxy resins themselves such as isopropylidenebisphenol-epichlorohydrin epoxy resins may be stabilized against degradation.

Hydrocarbons such as gasoline, kerosene, diesel fuel, fuel oil, furnace oil, and jet fuel may be effectively protected. Likewise, synthetic hydrocarbon lubricants, for example, α-decene trimer, polybutene lubricants, di and tri-$C_{12-30}$ alkylated benzene and naphthalene synthetic lubricants are likewise protected.

Organometallics such as tetraethyllead, tetramethyllead, tetravinyllead, ferrocene, methyl ferrocene, cyclopentadienyl magnesium tricarbonyl, methyl cyclopentadienyl magnesium tricarbonyl, cyclopentadienyl nickel nitrosyl, and the like, may be effectively protected against oxidative degradation. Silicone oils and greases may be also protected.

Synthetic ester lubricants such as those used in turbines and turbojet engines may be given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions mixtures of polyols, polycarboxylic acids, and aliphatic monocarboxylic acids and/or monohydric alkanols. An example of these complex esters is the condensation product formed from adipic acid, ethylene glycol and a mixture of $C_{5-9}$ aliphatic monocarboxylic acids. Plasticizers such as dioctyl phthalate may be effectively protected. Heavy petroleum fractions such as tar and asphalt may also be protected should the need arise.

Polyamides such as adipic acid-1,6-diaminohexane condensates and poly-6-aminohexanoic acid (nylon) may be effectively stabilized. Polyalkylene oxides such as copolymers of phenol with ethylene oxide or propylene oxide may be stabilized. Polyphenylene ethers such as poly-2,6-dimethylphenylene ether formed by polymerization of 2,6-dimethylphenol using a copper-pyridine or like catalyst may be stabilized. Polycarbonate plastics and polyformaldehyde resins may be also protected.

Linear polyesters such as phthalic anhydride-glycol condensates may be given a high degree of protection. Other polyesters such as trimellitic acid-glycerol condensates may be also protected. Polyacrylates such as polymethylacrylate and polymethylmethacrylate may be effectively stabilized. Polyacrylonitriles and copolymers of acrylonitriles with other olefinically unsaturated monomers such as methylmethacrylates may be also effectively stabilized.

The additives may be used to protect any of the many organic substrates to which an antioxidant is normally added. It may be used where economics permit to protect such substrates as asphalt, fluorocarbons such as Teflon, polyvinyl acetate, polyvinylidene chloride, coumarone-indene resins, polyvinyl ethers, polyvinylidene bromide, polyvinylbromide, acrylonitrile, vinyl bromide copolymer, vinyl butyral resins, silicones such as dimethylsilicone lubricants, phosphate lubricants such as tricresylphosphate, and the like.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

Other utilities for the compounds of this invention include their use as raw materials in the synthesis of polymers and as intermediates in the synthesis of pharmaceuticals, pesticides, herbicides, and the like.

The foregoing disclosure and description of the invention is illustrative and explanatory thereof and various changes in the illustrated compositions may be made within the scope of the appended claims without departing from the spirit of the invention.

What is claimed is:

1. A compound of the formula:

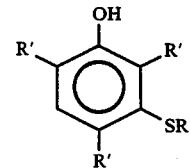

or a compound of the formula:

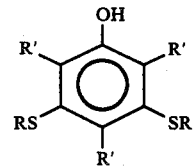

wherein the R' groups are the same or different hydrocarbyl groups and R is a hydrocarbyl group having up to about 10 carbon atoms.

2. A compound of claim 1 wherein R' groups are alkyl groups of 1 to 50 carbon atoms.

3. A compound of claim 2 wherein R is an alkyl group containing up to about 4 carbon atoms.

4. 2,4,6-trimethyl-3-(methylthio)phenol.

5. 2,4,6-trimethyl-3,5-bis(methylthio)phenol.

6. A compound of the formula:

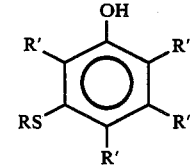

wherein the R' groups are the same or different hydrocarbyl groups and R is a hydrocarbyl group having up to about 10 carbon atoms.

7. A compound of claim 6 wherein R' groups are alkyl groups of 1 to 50 carbon atoms.

8. A compound of claim 7 wherein R is an alkyl group containing up to about 4 carbon atoms.

9. A process for making a compound of claim 6 said process comprising reacting a phenol having the formula:

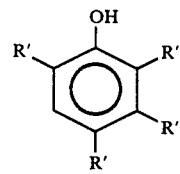

wherein the R' groups are the same or different hydrocarbyl groups with an excess of hydrocarbyl disulfide in the preence of an aluminum phenoxide catalyst at a temperature of 0°–300° C., the molar ratio of said catalyst to said disulfide being less than 1.

10. A process of claim 9 wherein said hydrocarbyl disulfide is an alkyl disulfide wherein each alkyl group is the same or different and contains 1 to about 6 carbon atoms.

11. A process of claim 10 wherein said temperature is about 100°–200° C.

* * * * *